US012303640B2

(12) United States Patent
Castellanos (10) Patent No.: US 12,303,640 B2
(45) Date of Patent: May 20, 2025

(54) ADMINISTERING APPARATUS WITH DISPENSING DEVICE SYSTEM FOR DELIVERY OF COMBUSTIBLE MEDICAMENTS

(71) Applicant: THE ORIGINAL SUSTAINABLE JOINT LLC, Bronx, NY (US)

(72) Inventor: Daniel Castellanos, Bronx, NY (US)

(73) Assignee: THE ORIGINAL SUSTAINABLE JOINT LLC, Bronx, NY (US)

( * ) Notice: Subject to any disclaimer, the term of this patent is extended or adjusted under 35 U.S.C. 154(b) by 967 days.

(21) Appl. No.: 17/386,514

(22) Filed: Jul. 27, 2021

(65) Prior Publication Data
US 2021/0393896 A1 Dec. 23, 2021

Related U.S. Application Data

(60) Provisional application No. 62/704,856, filed on May 31, 2020.

(51) Int. Cl.
| | |
|---|---|
| A61M 15/06 | (2006.01) |
| A24B 7/04 | (2006.01) |
| A61K 36/185 | (2006.01) |
| A61M 15/00 | (2006.01) |
| B02C 18/06 | (2006.01) |

(52) U.S. Cl.
CPC ............... *A61M 15/06* (2013.01); *A24B 7/04* (2013.01); *A61M 15/0025* (2014.02); *B02C 18/06* (2013.01); *A61K 36/185* (2013.01); *A61M 2205/75* (2013.01)

(58) Field of Classification Search
None
See application file for complete search history.

(56) References Cited

U.S. PATENT DOCUMENTS

| | | | |
|---|---|---|---|
| 2012/0138075 A1* | 6/2012 | Jespersen ................ | A24F 15/12 131/331 |
| 2012/0186592 A1* | 7/2012 | Schleider ................. | A24F 1/28 131/191 |
| 2013/0192620 A1* | 8/2013 | Tucker ................. | H05B 3/0014 131/329 |
| 2017/0367401 A1* | 12/2017 | Wrobel .................... | F23Q 7/02 |

OTHER PUBLICATIONS

DCOU, "DCOU Premium Aluminium Herb Grinder 2.2 Inches 4 Piece Metal Grinder with Pollen Catcher with Laser Flower Pattern (Pink)", selected images (Year: 2018).*
DCOU, "DCOU Premium Aluminium Herb Grinder 2.2 Inches 4 Piece Metal Grinder with Pollen Catcher with Laser Flower Pattern (Pink)", full webpage (Year: 2018).*
Fakespot, "Herb Grinder—Max Premium Quality Herb Grinder with Strong Grip—Aircraft Grade" (Year: 2019).*
"The Last Herb Grinder You Will Ever Want to Own", Infinium (Year: 2018).*

* cited by examiner

*Primary Examiner* — Michael H. Wilson
*Assistant Examiner* — Tobey C Le
(74) *Attorney, Agent, or Firm* — Wiggin and Dana LLP (57) ABSTRACT

The present invention relates to devices, systems, and methods wherein certain embodiments of the invention include, but are not limited to milling and dispensing, forming and administering, prescribed dosages of one or more combustible medicaments including medical cannabis, dried flower containing tetrahydrocannabinol (THC), dried flower containing cannabidiol (CBD), and hemp dried flower for inhalation and treatment of various conditions and indications.

19 Claims, 9 Drawing Sheets

ADMINISTERING APPARATUS WITH DISPENSING DEVICE SYSTEM FOR DELIVERY OF COMBUSTIBLE MEDICAMENTS

CROSS-REFERENCE TO RELATED APPLICATION

This application claims the benefit under 35 U.S.C. § 119(e) of U.S. Provisional Application No. 62/704,856 filed May 31, 2020, which is herein incorporated by reference in its entirety.

FIELD OF THE DISCLOSURE

The present invention relates to devices, systems, and methods wherein certain embodiments of the invention include, but are not limited to milling and dispensing, forming and administering prescribed dosages of one or more combustible medicaments including medical cannabis and hemp dried flower for inhalation and treatment of various conditions and indications.

BACKGROUND

The predominant mode of inhaling prescribed combustible medicaments, including cannabis and/or hemp cannabidiol in dried flower form, is through combustion by various methods such as via a rolled tobacco leaf or paper sleeve, pipe or pipette, or similar device, but not limited to the following methods described herein, including devices which may incorporate a filter.

The conventional method of inhaling prescribed hemp cannabidiol dried flower, for example, is by using cigarette rolling paper, cigar leaves, blunt wraps, and rolling paper, and pre-rolled hemp cigarettes shaped in a cylindrical or conical design whether hand-rolled or pre-rolled. The hand-rolling process requires steady hands, sharp eyesight, and a high degree of dexterity to perform the intricate steps necessary.

The first step when rolling prescribed hemp into a cigarette shape using standard cigarette rolling paper made by hemp or cotton rolling paper is to first fold the paper and then bend the paper into either a U or V shape to form a pouch in order to add and spread the dried flower evenly over the entire length of the V or U shaped semi-folded paper with one side taller than the opposite fold. The longer portion of the rolling paper is then bent and rolled over the portion of the rolling paper that has the dried flower. Once the paper is completely rolled, moistening the glue strip on the end seals it. The amount of cannabidiol inhaled by the patient is up to the patient's discretion making it difficult for physicians to monitor since the rolled hemp cigarette or cigar will contain amounts that were added by hand and less likely to be uniformed amounts inhaled with each draw.

One may add a hemp or cotton cigarette filter to mitigate impurities, tar and burnt ash particles from entering the airflow and jeopardizing the quality, taste and potency of each draw. The inclusion of a filter would require a person to add the filter during the folding process of hand rolling the rolling paper into a U or V shape. The filter would be added to one end of the rolling paper after the rolling paper is first folded into a V or U shape form but before adding the prescribed dried flower. Once the cigarette filter is added to one end of the folded paper in U or V shape form the prescribed hemp dried flower will be added and spread evenly in the U or V shape pouch fold, and then sealed by moistening the end of the rolling paper. While pre-rolled cigarettes may have filters, the selection of cigarettes having both a desired combustible medicament and a desired filter type may be limited, forcing the patient to make undesired compromises on their treatment regimen.

Conventional methods to inhale prescribed hemp cannabidiol dried flower by combustion use either hand-rolled cigarette rolling papers or pre-rolled hemp cigarettes, cigars, or blunt wraps, but these methods are inadequate because the papers used, i.e. cigarette rolling papers, cigars and blunt wraps, add unnecessary impurities to inhale that provide no additional benefit to the patient, and in some cases may have deleterious effect. Moreover, these conventional methods provide no accurate way for a physician or user to monitor and measure the amount drawn. These hand-rolled and pre-rolled methods using the various paper forms also do not include filters or additional means to prevent tar and ash particles from being entrained during inhalation thereby contaminating the inhaled airflow. Some rolling papers may come affixed with an additional feature for filtration. For example, U.S. Pat. No. 5,657,773 recites a cigarette rolling paper provided with a rectangular strip of material attached thereto. The rectangular strip rolls into a spiral support within the rolled paper to assist with rolling and to filter the rolled cigarette for inhalation of large particles of combusted medicament. While the included spiraled support material helps to mitigate some of the larger combusted particles from being inhaled, the support fails to sufficiently filter the inhaled dosage of smaller particles of undesired inhalants, such as tar and ash. Furthermore, the rolling paper and filter paper directly add unnecessary impurities to inhale, which provide no additional benefit to the patient.

Another method for inhaling prescribed hemp in dried flower form is with the use of a single dose smoking pipe and more particularly with a one-hitter pipe also known as a "bat" (which is a pipe designed to resemble a miniature baseball bat or other cylindrical apparatus) that provides a single dose for inhalation from dried flower packed into an unregulated bowl. Single dose smoking devices such as bats and one-hitter pipes allow users to stuff varying amounts of hemp dried-flower into the one-hitter pipe's bowl. The amount of hemp packed into the bowl is at the patient's discretion. Due to these deficiencies, it is difficult for the patient to obtain a desired dosage leading to either insufficient treatment or potentially a larger than intended dose which may have deleterious and unintended psychoactive effects. These disadvantages mean that a patient may experience inconsistent and undesired treatment outcomes.

Similarly, filtered single-dose smoking pipe products such as one-hitter pipes and bats currently provide some filtration yet use the same cigarette filters used in hand-rolling methods and systems that disrupt airflow and mitigate the amounts inhaled because of the tight airflow design of the filters. Single-dose devices such as one-hitter pipes and bats, also lack precision dispensing capabilities required to dispense dosages in accordance with prescriptions because they lack the measurable dispensing capabilities necessary for physicians to better monitor patient use and effects per dosage. For example, the Easy Hitter of US Pat. Pub. No 2010/0078035 A1 does not limit the storage amount within its bowl creating a disadvantage of an unregulated bowl which means doses will not be uniform and therefore, not monitorable by physicians. Accordingly, there is a need for a device that solves this problem and has the capability to deliver fresh uniform doses.

An embodiment may relate to filters added to hand-rolled rolling-paper, pipes, one-hitters, and filtered systems and methods. Conventional cigarette filters are made up of either natural and biodegradable materials that include certain embodiments in the present invention, but not limited to unrefined cotton, or plant based cellulose, while other conventional cigarette filters used may include fibrous materials such as acetate tow or a carbon-based filtering material. Cigarette filters when made in the standard cylindrical shape and form using natural, or biodegradable materials, or chemically infused with smoke constituent adsorbents tends to mitigate airflow that disrupts the intended draw per dosage. While these filters provide some protection against cross-contamination from ash debris reentering the airflow, the design also inhibits airflow forcing patients to draw much harder pull's which defeats the purpose for the intended system and method thus permitting entrained fine ash particles. For example, U.S. Pat. No. 6,779,529 B2 discloses a cigarette filter with a blunt solid design that mitigates airflow. While the disclosed filter structure provides some filtration, its overall design may in fact allow for impurities to become entrained from the variety of absorbents included while mitigating the airflow and inadvertently impacting the intended outcome. There is a need to provide a cleaner solution for filtering more fine particles without inadvertently adding harmful ingredients. Although not designed for smoking devices, the frustoconical portion of the vacuum cleaning apparatus recited in U.S. Pat. No. 5,160,356 improves fine particle capture without mitigating airflow because its design creates centrifugal forces that help force fine particles onto to the sides as the airflow funnels into the conical design. The conical shape was adapted and refined in the current invention in order to improve the filtration design part without mitigating the airflow.

In the present invention, the embodiment of the frustoconical and spiral shaped filter is based on a vacuum cyclone filter that has an advantageous capability of filtering by centrifugal forces. The centrifugal forces are created in the presence of a vacuum because the suction from each inhalation pulls dirt particles into the frustoconical opening but not through the smaller aperture of the filter. Fine particles enter the frustoconical filter because the forces generated by each subsequent inhalation on the pipette creates centrifugal forces within the frustoconical-designed-filter forcing the dirt and fine particles to collect on the sides of the filter thereby maintaining a consistent airflow while keeping the bores passage unblocked.

The following description relates to a conventional herb grinder, in particular to a hand-grinder device and a method for bringing hemp dried-flower into physical form suitable for inhalation. A user of the conventional hand-grinder needs to discern an appropriate quantity to grind in consideration of the effects one can expect. A disadvantage of conventional grinders, such as the leaves and seeds hand grinder disclosed in US Pat. Pub. No. 20080191073 A1, is the lack of a precision administering and dispensing chamber for delivering uniform fine ground prescribed hemp dried flower. A second disadvantage is in relation to the first disadvantage for lack of uniformity for delivery of prescribed hemp dried flower dosages.

The delivery device part disclosed in US Pat. Pub. No. 20170196775 A1 increases the accuracy when delivering liquid medication. In some embodiments the device has threads on the perimeter of the delivery device. The present invention adapts and refines the above device to improve the dispensing capabilities of the conventional grinder for patients who need a regulated dosage dispenser.

Lastly, the smoking system also commonly known as a dugout allows for storage of undisclosed amounts and unregulated amounts for packing one-hitters. While this approach may be adequate for hemp dried flower personal users, such as taught in U.S. Pat. No. 4,214,658, this approach also lacks the required capability to also be monitored by physicians.

There are several disadvantages in association with the devices, systems, and methods for administering and dispensing prescribed hemp dried-flower for inhaling by combustion prescribed hemp dried flower in self-rolled or pre-rolled cigarettes, hollowed out cigars, blunt wraps, or one-hitter pipes (e.g. pipes fashioned in a shape similar to a baseball bat), pipes designed after a cigar or cigarette, or fashioned in other design shapes and forms not currently mentioned but not limited to the aforementioned devices. Patients who are prescribed hemp dried-flower for combustible inhalation are left to discern the amount for each dosage based on trial and error with every device, system and method mentioned above herein. Another disadvantage is that conventional means of inhaling prescribed hemp dried flower lacks the capability to deliver a predetermined amount for inhalation as one would when prescribed medicine in pill form or liquid form (e.g. take one pill daily, take two tablespoons, etc.).

It would be desirable to provide an inhaling apparatus, system, and method that is disposed to administer and dispense prescribed dosages of hemp cannabidiol dried flower for inhalation. In some embodiments, the described devices may permit the use of replaceable, disposable cigarette filters and in particular natural plant cellulose frustoconical spiraled filters therein. Such apparatuses, systems, and methods provide for customizability and optimization of treatments involving combustible medicaments, in turn solving the various described problems and shortcomings with known apparatuses, systems, and methods.

SUMMARY

Accordingly, objects of the present invention provide improvements of certain embodiments in order to deliver precision administering of prescribed hemp cannabidiol dried flower for inhalation via filtered pipette.

Another embodiment of the present invention is a milling device, system and method for grinding, and then dispensing prescribed hemp cannabidiol dried flower for inhalation when conjoined with the prior embodiment for delivering prescribed dosages with greater accuracy that eliminates waste.

Another embodiment of the present invention is the scent sealing lock-cap designed to lock into the front of the inhaling apparatus, and in particular, into the administering pipette threaded bowl chamber on the front end of the pipette.

Another embodiment of the present invention is the pipette threaded administering bowl for delivery of prescribed dosages of hemp dried-flower to work in conjunction with the milling and dispensing device prior to bring prescribed dried flower into specific forms for inhalation.

Another embodiment of the present invention is the notch scored within the pipette threaded administering bowl chamber that creates an indentation whereby a stainless-steel dispensing and filtering-screen locks into the notch of the bowl intended for the filter screen. The etched groove holds the stainless-steel filter-screen in place to mitigate fine ash particles from being entrained into the airflow. The stainless-steel filter-screen locked into the notch within the pipette bowl also functions as part of the system and method for bringing prescribed hemp dried flower to administering form when conjoined with the dispensing chamber of the ground flower canister of the dispensing chamber of the herb grinder.

Another embodiment of the present invention is the filter device chamber system and method within the second half of the invention that connects to the first half of the inventions embodiment. The embodiment of the second half of the invention is the frustoconical spiral filter and the filter chamber that allows the filter to capture fine ash particles and tar resin without hindering the airflow within the bore.

Another embodiment of the present invention is the extended cooling mouthpiece. The extended cooling mouthpiece is attached to the second-half of the present inventions filter-chamber. The extended cooling mouthpiece with narrow bore attached to the rear of the filter chamber of the second half of the present invention is for inhaling a cooler draw. The embodiment of the frustoconical filter allows it to remove impurities such as fine ash particles and tar resin without hindering the airflow during inhalation.

Another embodiment of the present invention is the push-pin bore-cleaner for inserting the stainless-steel filter-screen into the base of the pipette administering bowl chamber to set the pushed filter screen into position in the etched ring scored into the base of the administering bowl in order to lock in the filter screen, and the cleaner-pin is also for clearing out the bore connected to the pipette bowl and bored mouthpiece, and for pushing-out and removing the spent stainless steel dispensing and filter-screen from the pipettes dried-flower administering bowl.

DETAILED DESCRIPTION

Many of the embodiments described herein are improvements for apparatuses, systems and methods related to inhaling a dosage of a combustible medicament, such as hemp dried flower and/or cannabis products that the specification will describe. In particular, described are the parts of the process and devices to which the improvements relate, and to the specific improvements and to such parts and disclosure as necessary for a complete understanding of the invention. The embodiments described herein are not limited to the precise forms and methods disclosed in the following detailed description.

Definitions

As used herein, the term "combustible medicament" may be used to describe any material that is used with the milling and dispensing devices and/or pipe devices of the present disclosure. In some embodiments, a "combustible medicament" may comprise any combustible material safe or desirable for inhalation upon combustion using a lighter, flame, or other heat source. In some embodiments, the "combustible medicament" is not necessarily a medically prescribed material and may be an over-the-counter, recreational, herbal, homeopathic, hemp, cannabis, marijuana, tobacco, and/or other material. In some embodiments, a "combustible medicament" may further comprise an additional active agent, filler, combustion-assistive substance, or other additives that would be desirable as understood by a person of skill in the art. In some embodiments, the milling and dispensing devices and pipes herein are specifically useful for dispensing a desired and/or prescribed dosage of marijuana flower as the "combustible medicament". In some embodiments, the "combustible medicament" may be selected from the group consisting of cannabis flower, hemp flower, marijuana flower, CBD flower, and combinations thereof. In some embodiments, the marijuana flower is medically-prescribed. Cannabis flower and/or marijuana flower may be used with the devices, systems, and methods of the present disclosure in accordance with any pertinent local, state, or federal regulations.

In some embodiments, the cannabis flower or marijuana flower is dried and has a water content of approximately about 5 to about 12 wt %. In some embodiments, cannabis flower or marijuana flower has a THC content of about 5 wt % to about 25 wt % and a CBD content of about 5 wt % to about 25 wt %. Because the prescribed dosage of cannabis flower or marijuana flower may be different depending upon the THC and/or CBD content, and may further depend upon the condition being treated, the dosage dispensing devices of the present disclosure may be configured to accommodate varying dosage amounts. In some embodiments, the dosage dispensing chamber may have one or more markings for measurement of various dosages. In some embodiments, more than one ground flower canisters may be supplied each having different dosage dispensing chamber volumes controlled by depth, radius/diameter, or combinations thereof. In an alternative embodiment, inserts may be provided that narrow the dosage dispensing chamber to alter the volume. In embodiments having varying dosage dispensing chamber dimensions, the pipe front half and/or administration bowl may have correspondingly configured dimensions such that the administration bowl fits within the dosage dispensing chamber. These and further embodiments will become apparent from the present disclosure.

The terms "grinder" and "mill", "grinding" and "milling", and "to grind" and "to mill" are used synonymously and interchangeably throughout this disclosure. The "milling and dispensing devices" of the present disclosure may be referred to simply as "mill" in the singular or "mills" in the plural. Use of "mill" in the singular does not limit described components or characteristics to the embodiment described, which may be generally applied to any "mills" or "milling and dispensing devices" of the present disclosure, as would be understood by a person of skill in the art.

The terms "pipette" and "pipe" are used synonymously and interchangeably throughout this disclosure and are used to describe an embodiment of an administration device. A pipette provides a measured dose for administering medicine and typically has a first end with a mouthpiece from which the patient inhales while a combustible medicament in an administration bowl at a second end is combusted with an open flame, heat, or any appropriate combustion method. In some embodiments, a pipette may comprise more than one piece, said pieces being engageable. In some embodiments, a pipette may comprise one or more filters in an internal chamber to filter the administered dosage inhaled. In an embodiment, the pipette, and particularly the end thereof comprising an administration bowl, is configured and dimensioned to fit within a dosage dispensing cavity of a milling and dispensing device. Various alternative embodiments for a pipette, as well for any appropriate administration device for use with milling and dispensing devices, are contemplated.

The term "patient" describes a mammalian or, preferably, human subject receiving one or more doses of a combustible medicament. The "patient" may be desirous of, in need of, or otherwise eligible for one or more doses of a combustible medicament. The "patient" may be prescribed one or more doses of a combustible medicament by a physician or health care professional. In some embodiments, the patient may be suffering from one or more conditions selected from the group consisting of cancer, HIV infection or AIDS, amyotrophic lateral sclerosis (ALS), Parkinson's disease, multiple sclerosis, spinal cord injury with spasticity, epilepsy, inflammatory bowel disease, neuropathy, Huntington's disease, post-traumatic stress disorder, severe or chronic pain, pain that degrades health and functional capability as an alternative to opioid use or substance use disorder, cachexia or wasting syndrome, severe nausea, seizures, severe or persistent muscle spasms, opioid use disorder, glaucoma, Crohn's disease, sickle cell disease, post laminectomy syndrome with chronic radiculopathy, severe psoriasis and psoriatic arthritis, ulcerative colitis, complex regional pain syndrome type I and type II, cerebral palsy, cystic fibrosis, terminal illness requiring end-of-life care, spasticity or neuropathic pain associated with fibromyalgia, severe rheumatoid arthritis, post herpetic neuralgia, hydrocephalus with intractable headache, intractable headache symptoms, neuropathic facial pain, muscular dystrophy, osteogenesis imperfecta, interstitial cystisis, median arcuate ligament syndrome, vulvodynia and vulval burning, Tourette syndrome, and Ehlers-Danslos syndrome associated with chronic pain. In some embodiments, the patient may be desirous of or requiring treatment for any other physical, psychological, or neurologic condition for which a combustible medicament may provide treatment or relief. In some embodiments, a patient desires a psychoactive effect of a combustible medicament without suffering from any definable conditions.

The term "kief" as used herein typically refers to any particles sifted from cannabis flower through a mesh screen or sieve. "Kief" may refer to crystals or loose resin trichomes cannabis that are freed from the cannabis flower upon agitation or, more typically, grinding. The "kief" may comprise higher levels of THC and other psychoactive cannabinoids than the flower material and may therefore be dosed differently. In some embodiments, kief may be used separately from or in combination with a combustible medicament as desired or prescribed. In some embodiments, the kief is undesired and may be discarded.

The term "dose" as used herein relates generally to an amount of a combustible medicament to be administered to a patient. In some embodiments, the term "dose" refers to a weight, volume, or amount of a combustible medicament such as cannabis flower. In some embodiments, the term "dose" refers to a weight of a component of a combustible medicament, such as THC, CBD or another component of cannabis flower. In some embodiments, the dose is about 0.5 mg, or about 1 mg, or about 1.5 mg, or about 2 mg, or about 2.5 mg, or about 3 mg, or about 3.5 mg, or about 4 mg, or about 5 mg, or about 6 mg, or about 7 mg, or about 8 mg, or about 9 mg, or about 10 mg or more. In some embodiments, the dose is formulated with one or more excipients in a pharmaceutical composition. In some embodiments, the dose is compressed with or without excipients to form a combustible pill or pellet. In some embodiments, the dose is administered as-necessary. In some embodiments the dose is administered at certain time spacings such as every hour, every two hours, every three hours, every four hours, every five hours, every 6 hours, etc. In some embodiments, the dose is administered daily. In some embodiments, the dose is administered in varying amounts depending upon the severity of symptoms or at the discretion of the patient or health care provider.

Milling and Dispensing Devices

Figure 1:
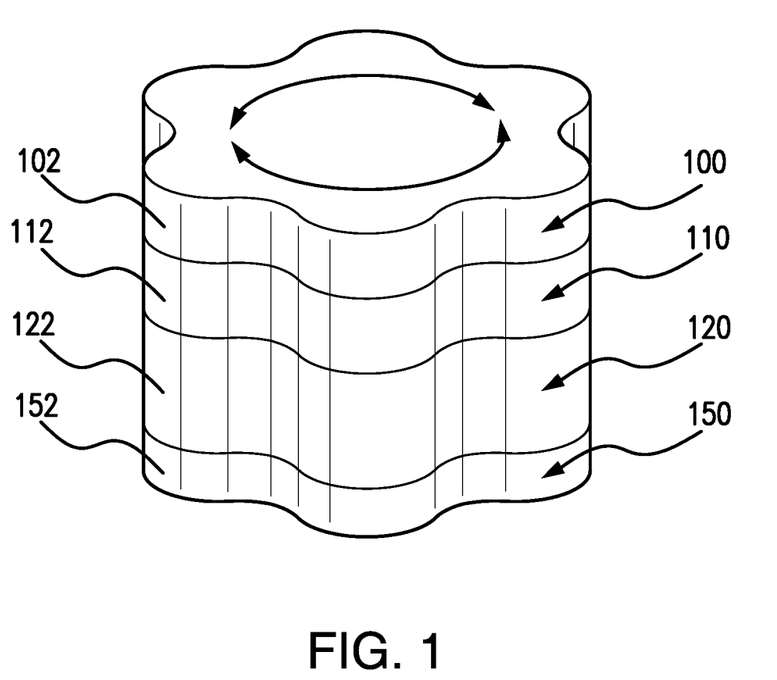
FIG. 1 is a perspective view of an embodiment of an assembled milling and dispensing apparatus.

As illustrated in FIG. 1, a mill may comprise multiple components, including but not limited to a top grinder plate 100, a bottom grinder plate 110, a ground flower canister 120, and a kief extract canister 150. In some embodiments, the top grinder plate 100 and bottom grinder plate 110 are rotatably engaged. In some embodiments, the top grinder plate 100 and bottom grinder plate 110 are magnetically and rotatably engaged. In some embodiments, the top grinder plate 100 and bottom grinder plate 100 can be placed in any orientation because of the rotatable engagement. In some embodiments, the top grinder plate 100 may have an ergonomic outer contour such that the plate may be easily grasped. In some embodiments, the top grinder plate 100 may have one or more knobs 102 defined by the outer contour of the grinder plate 100. In some embodiments, the bottom grinder plate 110 may have an ergonomic outer contour such that the plate may be easily grasped. In some embodiments, the bottom grinder plate 110 may have one or more knobs 112 defined by the outer contour of the grinder plate 110. In some embodiments, the knobs 102 of the top grinder plate 100 and the knobs 112 of the bottom grinder plate 110 may be oriented in any orientation because of the rotatable engagement between the top grinder plate 100 and bottom grinder plate 110.

In some embodiments, the bottom grinder plate 110 and ground flower canister 120 are threadably engaged. In some embodiments, the bottom grinder plate 110 and ground flower canister 120 are engaged by a locking mechanism that is lockable and/or engageable by rotation in one direction and releasable by rotation in the opposite direction. In some embodiments, the engagement between the bottom grinder plate 110 and ground flower canister 120 is aligned or alignable such that the two components are oriented in a particular orientation with respect to each other when engaged. In some embodiments, the ground flower canister 120 may have an ergonomic outer contour such that the canister may be easily grasped. In some embodiments, the ground flower canister 120 may have one or more knobs 122 defined by the outer contour of the canister 120. In some embodiments, the knobs 112 of the bottom grinder plate 110 and the knobs 122 of the ground flower canister 120 are aligned or alignable such that the two components are oriented in a particular orientation with respect to each other when engaged. In some embodiments, the desired orientation is such that the knobs 112 and 122 are substantially or fully overlapping.

In some embodiments, the ground flower canister 120 and kief extract canister 150 are threadably engaged. In some embodiments, the ground flower canister 120 and kief extract canister 150 are engaged by a locking mechanism that is lockable and/or engagable by rotation in one direction and releasable by rotation in the opposite direction. In some embodiments, the engagement between the ground flower canister 120 and kief extract canister 150 is aligned or alignable such that the two components are oriented in a particular orientation with respect to each other when engaged. In some embodiments, the kief extract canister 150 may have an ergonomic outer contour such that the canister may be easily grasped. In some embodiments, the kief extract canister may have one or more knobs 152 defined by the outer contour of the canister 150. In some embodiments, the knobs 122 of the ground flower canister 120 and the knobs 152 of the kief extract canister 150 are aligned or alignable such that the two components are oriented in a particular orientation with respect to each other when engaged. In some embodiments, each of the knobs 112 of the bottom grinder plate 110 and the knobs 122 of the ground flower canister 120 and the knobs 152 of the kief extract canister 150 are aligned or alignable such that the three components are oriented in a particular orientation with respect to each other when engaged. In some embodiments, the desired orientation is such that the knobs 112 and 122 and 152 are substantially or fully overlapping.

Figure 2:
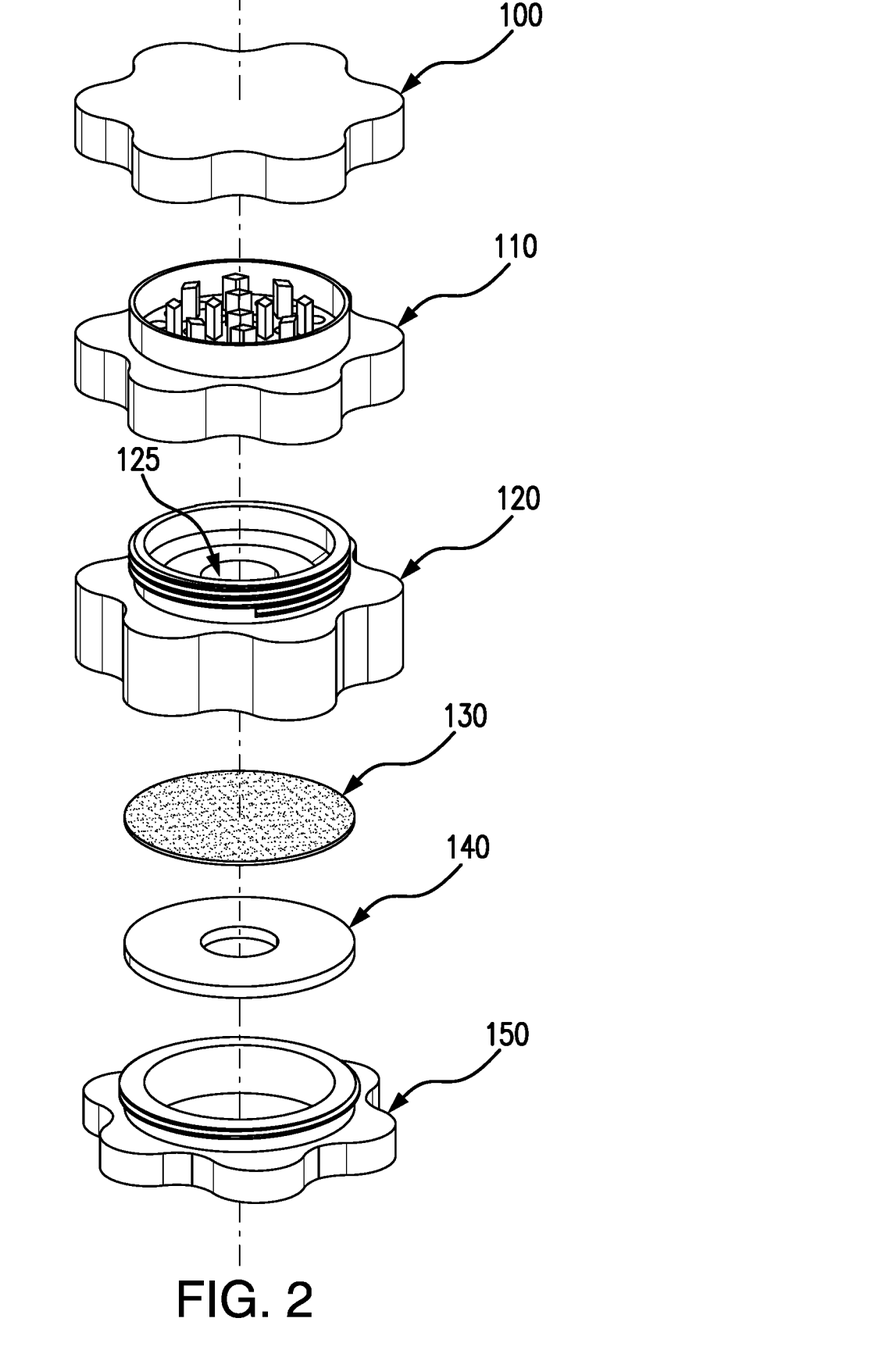
FIG. 2 is an exploded perspective view of an embodiment of a milling and dispensing apparatus.

An embodiment is illustrated in FIG. 2 showing an exploded perspective view of a mill comprising several components. From top-to-bottom, the pieces shown are a top grinder plate 100, a bottom grinder plate 110, a ground flower canister 120, a dosage dispenser and kief extractor 130 (alternatively referred to as a "screen" 130), a retaining washer 140, and a kief extract canister 150. The ground flower canister 120 has a dispensing chamber 125 continuous through its axial dimension. The kief extractor 130 is retained against the bottom of the ground flower canister 120 by retaining washer 140, resulting in the bottom of the dispensing chamber 125 being defined by the kief extractor 130. The kief extractor 130 and retaining washer 140 are removable and/or replaceable for cleaning and/or maintenance of the mill. The bottom of the ground flower canister 120 may comprise a notch for seating the kief extractor or screen 130. In an alternative embodiment, the washer 140 is omitted and the kief extract chamber is configured and dimensioned to retain the kief extractor 130 in position against the bottom of the dispensing chamber 125 when the kief extract canister 150 and ground flower canister 120 are engaged.

In another alternative embodiment, the bottom of the dispensing chamber 125 of the ground flower canister 120 is defined by the body of the ground flower canister 120 such that the dispensing chamber 125 is not continuous through the axial dimension thereof. In such an embodiment, the mill may comprise a top grinder plate 100, a bottom grinder plate 110, and a ground flower canister 120 having a dispensing chamber 125 formed at a certain depth therein, and the kief extractor 130, washer 140, and kief extract canister 150 may be omitted.

Figure 3:
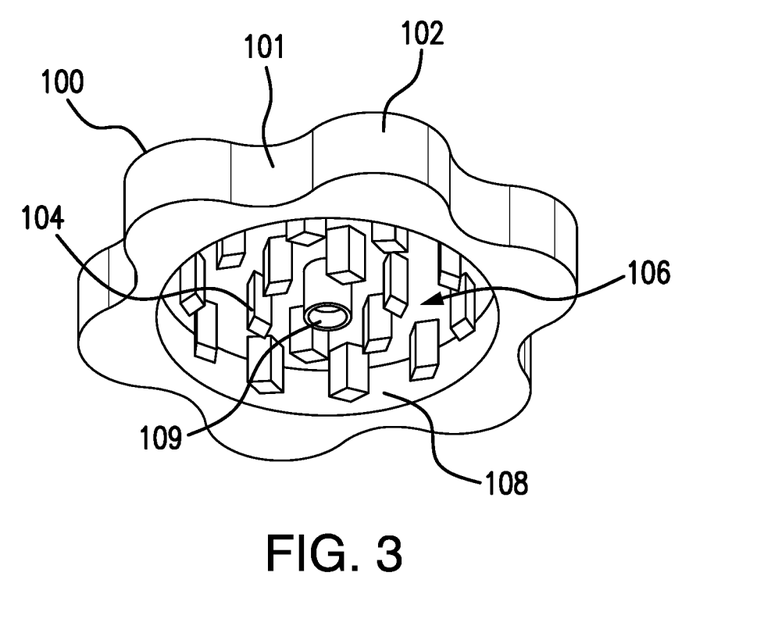
FIG. 3 is a perspective view of an embodiment of a grinder or mill top plate.

An exemplary embodiment of a top grinder plate is illustrated in FIG. 3. In some embodiments, the top grinder plate 100 may comprise, on its outer perimeter, one or more knobs 102 defined by one or more divots 101. In some embodiments, the outer perimeter may comprise no knobs or divots and may be circular. In some embodiments, the outer perimeter may be knurled or textured, or may alternatively comprise added grips for ease of operation. Such ergonomic features are particularly advantageous for individuals having limited grasping capacity or dexterity, such as arthritis patients, patients suffering from neurologic conditions, patients suffering from an injury or chronic condition, and the like.

The top grinder plate generally has a recessed chamber 106 on its bottom comprising one or more grinding or cutting blades 104. The grinding or cutting blades 104 may be arranged in a concentric orientation, each ring of grinding or cutting blades 104 having a particular radius from the center of the plate. In some embodiments, the recessed chamber 106 may be defined on its outer perimeter by a rim 108. In some embodiments, the center of the recessed chamber 106 comprises a central protrusion 109 having a magnet. In some embodiments, the magnet of the protrusion 109, bottom of the top grinder plate 106, and bottom of each grinding or cutting blade 104 are approximately level with one another.

Figure 4:
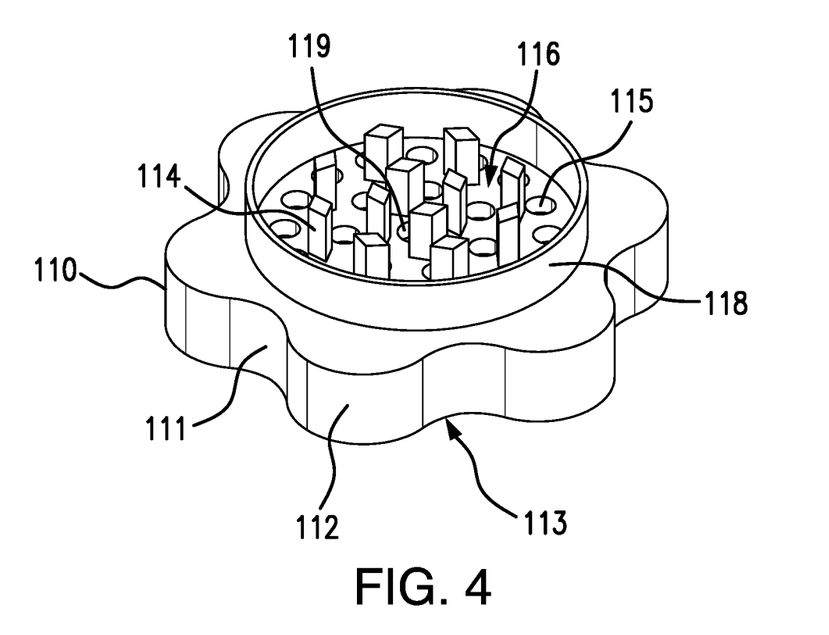
FIG. 4 is a perspective view of an embodiment of a grinder or mill bottom plate.

An exemplary embodiment of a bottom grinder plate is illustrated in FIG. 4. In some embodiments, the bottom grinder plate 110 may comprise, on its outer perimeter, one or more knobs 112 defined by one or more divots 111. In some embodiments, the outer perimeter may comprise no knobs or divots and may be circular. In some embodiments, the outer perimeter may be knurled or textured, or may alternatively comprise added grips for ease of operation. Such ergonomic features are particularly advantageous for individuals having limited grasping capacity or dexterity, such as arthritis patients, patients suffering from neurologic conditions, patients suffering from an injury or chronic condition, and the like.

The bottom grinder plate generally has a chamber 116 comprising one or more grinding or cutting blades 119. In some embodiments, the chamber 116 is defined by a protruding rim 118. In some embodiments, the protruding rim 118 has a diameter slightly smaller than and complimentary to the rim 108 of the top grinding plate 100 such that the protruding rim 118 fits inside of the rim 108 such that the top grinder plate 100 and bottom grinder plate 110 remain rotatable. The chamber 116 typically comprises one or more holes 115 disposed on the bottom of the chamber that allow ground material having a size smaller than the hole to pass through as the material is ground. At its center, the chamber 116 may comprise a magnet 119 for magnetic engagement with the magnet of the protrusion 109 of the top grinder plate 100. In some embodiments, the bottom of the grinder plate (not visible) may comprise a bottom cavity defined on its outer perimeter by threads for threaded engagement with the ground flower canister 120.

Figure 5:
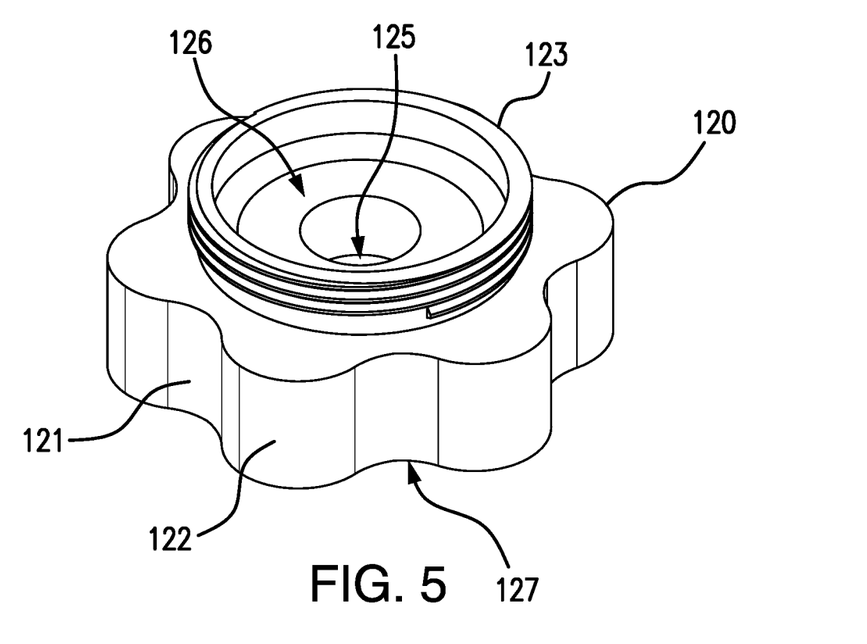
FIG. 5 is a perspective view of an embodiment of a ground flower canister having a dispensing chamber.

An exemplary embodiment of a ground flower canister is illustrated in FIG. 5. In some embodiments, the ground flower canister 120 may comprise, on its outer perimeter, one or more protrusions or knobs 122 defined by one or more depressions or divots 121. In some embodiments, the outer perimeter may comprise no protrusions or depressions and may be circular. In some embodiments, the outer perimeter may be knurled or textured, or may alternatively comprise added grips for ease of operation. Such ergonomic features are particularly advantageous for individuals having limited grasping capacity or dexterity, such as arthritis patients, patients suffering from neurologic conditions, patients suffering from an injury or chronic condition, and the like.

The ground flower canister 120 generally comprises a dispensing chamber 125 shaped as a cylindrical hole through the ground flower canister. In some embodiments, the dispensing chamber is centered in the ground flower canister 120. In some embodiments, the ground flower canister 120 may comprise a top chamber 126 defined by an outer rim 123. In some embodiments, the outer rim may be threaded and configured and dimensioned for threaded engagement with the bottom grinder plate 110.

In some embodiments, the outer rim 123 has a diameter of about 10 mm to about 150 mm, or from about 20 mm to about 80 mm, or from about 25 mm to about 60 mm, or from about 30 mm to about 50 mm, or from about 35 mm to about 45 mm. In some embodiments, the outer rim 123 has a diameter of about 10 mm, or about 12 mm, or about 15 mm, or about 17 mm or about 20 mm, or about 25 mm, or about 30 mm, or about 35 mm, or about 40 mm, or about 45 mm, or 50 mm, or about 55 mm, or about 60 mm, or about 65 mm, or about 70 mm, or about 75 mm, or about 80 mm, or about 85 mm, or about 90 mm, or about 95 mm, or about 100 mm, or about 125 mm, or about 150 mm.

In some embodiments, the dispensing chamber 125 has a diameter from about 5 mm to about 20 mm, or from about 7 mm to about 15 mm, or from about 9 mm to about 13 mm, or from about 10 mm to about 12 mm. In some embodiments, the dispensing chamber 125 has a diameter of about 5 mm, or about 6 mm, or about 7 mm, or about 8 mm, or about 9 mm, or about 10 mm or about 11 mm, or about 12 mm, or about 13 mm, or about 14 mm, or about 15 mm, or about 16 mm, or about 17 mm, or about 18 mm, or about 19 mm, or about 20 mm.

In some embodiments, the depth of the dispensing chamber 125 from the surface of the top chamber 126 to the screen 130 is from about 3 mm to about 30 mm, or from about 4 mm to about 20 mm, or from about 5 mm to about 10 mm, or from about 6 mm to about 8 mm. In some embodiments, the depth of the dispensing chamber 125, from the surface of the top chamber 126 to the screen 130, is about 3 mm, or about 3.5 mm, or about 4 mm, or about 4.5 mm, 5 mm, or about 5.5 mm, or about 6 mm, or about 6.5 mm, or about 7 mm, or about 7.5 mm, or about 8 mm, or about 8.5 mm, or about 9 mm, or about 10 mm, or about 12 mm, or about 14 mm, or about 15 mm, or about 20 mm, or about 25 mm, or about 30 mm.

In some embodiments, the other components of the mill are configured and dimensioned to appropriately accommodate the desired dimensions of the dispensing chamber, as would be understood to a person of skill in the art.

In some embodiments, the bottom of the ground flower canister (not visible) may comprise a bottom cavity defined on its outer perimeter by threads for threaded engagement with the kief extract canister.

Figure 6:
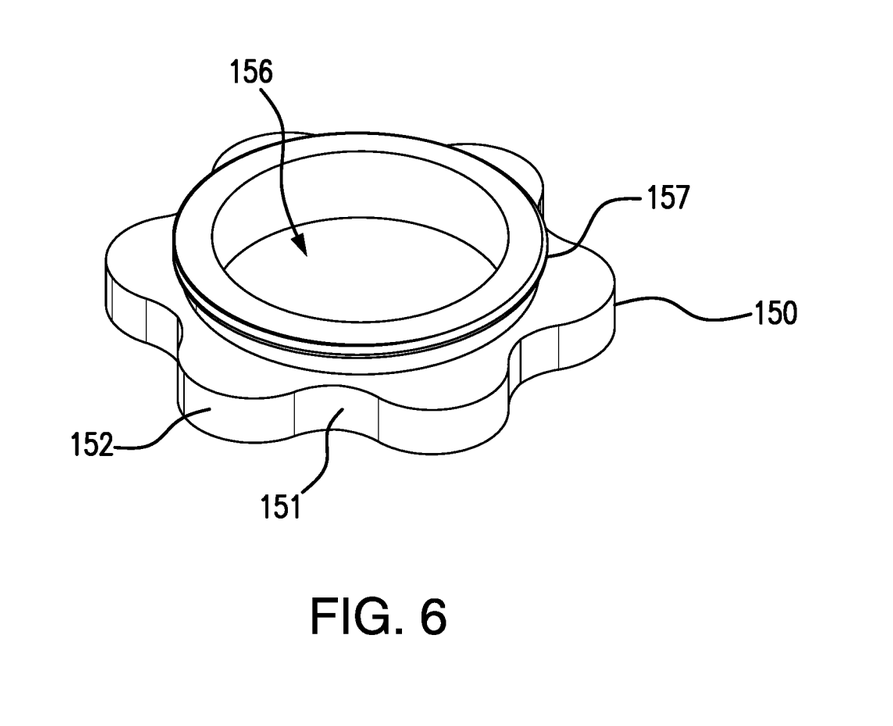
FIG. 6 is a perspective view of an embodiment of a kief extract canister.

An exemplary embodiment of a kief extract canister is illustrated in FIG. 6. In some embodiments, the kief extract canister 150 may comprise, on its outer perimeter, one or more knobs 152 defined by one or more divots 151. In some embodiments, the outer perimeter may comprise no knobs or divots and may be circular. In some embodiments, the outer perimeter may be knurled or textured, or may alternatively comprise added grips for ease of operation. Such ergonomic features are particularly advantageous for individuals having limited grasping capacity or dexterity, such as arthritis patients, patients suffering from neurologic conditions, patients suffering from an injury or chronic condition, and the like.

In some embodiments, the kief extract canister 150 may comprise a cavity 156 defined fully or partially by an outer rim 157. In some embodiments, the outer rim 157 is threaded for engagement with the ground flower canister 120. In some embodiments, the kief extract canister may be lined with a polymeric material for ease of kief removal and cleaning.

In some embodiments, the top grinder plate, bottom grinder plate, ground flower canister, and kief extract canister may have zero, or one, or two, or three, or four, or five, or six, or seven, or eight, or nine, or ten knobs. In some embodiments, a wrench or stand configured and dimensioned to accept the outer perimeter pattern of any portion of the mill may be included for ease of operation.

Pipes, Pipettes, and Administration Devices

Figure 7:
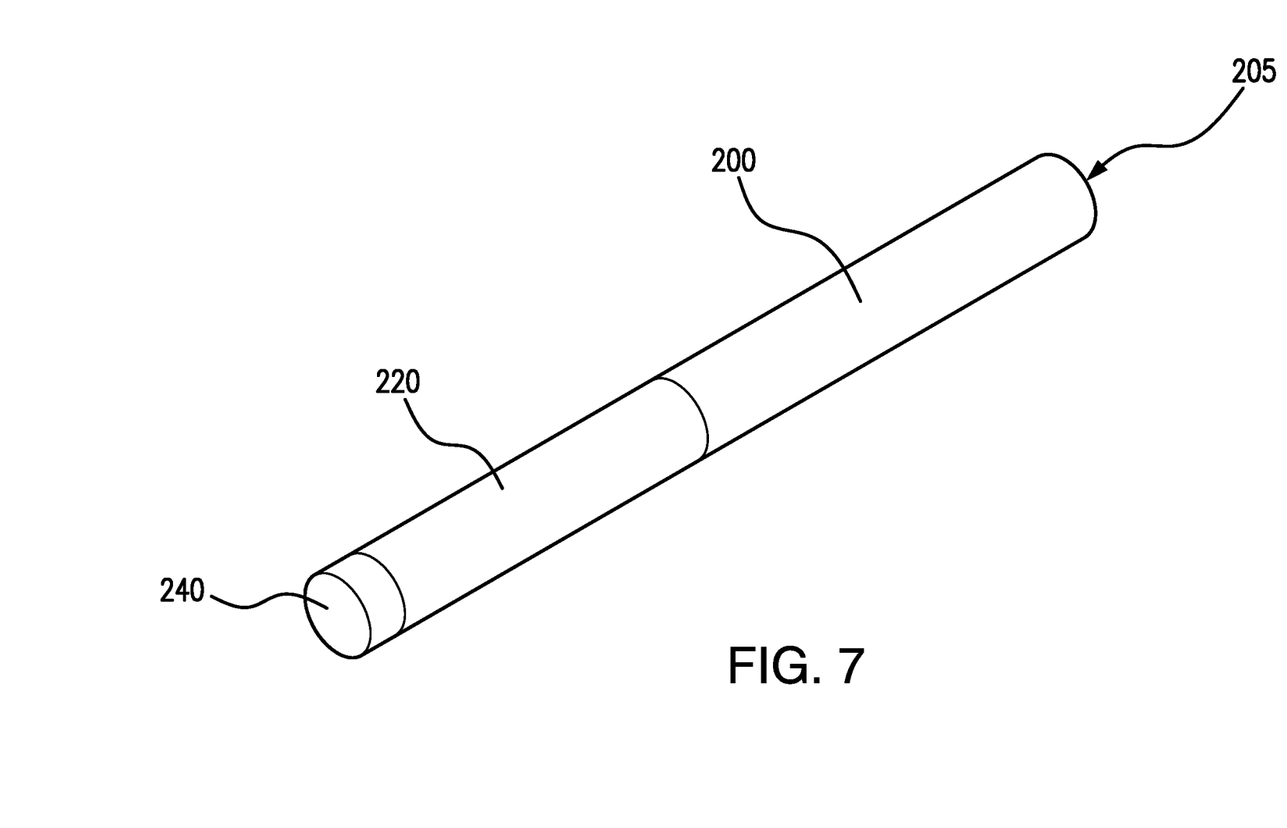
FIG. 7 is a perspective view of an embodiment of an assembled pipette administration device.

In some embodiments, described herein are pipettes for use with milling and dispensing devices. An embodiment of a pipette assembly is shown in FIG. 7. A pipette may comprise one or more pieces. A pipette may be comprised of one piece. A pipette may be comprised of one, two, three, four, five, or more pieces that can be assembled for use and disassembled for cleaning, maintenance, and the like. A pipette may comprise three pieces. A pipette may comprise an aeration and filtration chamber 200 having at its end a mouthpiece and inhalation hole 205, a pipette front half 220 and a cap 240. In some embodiments, the aeration and filtration chamber 200 is engaged with the pipette front half 220 at one end of the pipette front half 200 and the cap is engaged with the other end of the pipette front half 200. In some embodiments, the aeration and filtration chamber 200 is threadably engaged with the pipette front half 220 at one end of the pipette front half 200 and the cap is threadably engaged with the other end of the pipette front half 200. In some embodiments, the aeration and filtration chamber 200 removably engaged by press-fitting with the pipette front half 220 at one end of the pipette front half 200 and the cap is removably engaged by press-fitting with the other end of the pipette front half 200. In some embodiments, the aeration and filtration chamber 200 is threadably with the pipette front half 220 at one end of the pipette front half 200 and the cap is removably engaged by press fitting with the other end of the pipette front half 200. It can be appreciated that any method or manner of engagement between the pipette pieces is contemplated as would be understood by a person of skill in the art.

Figure 8:
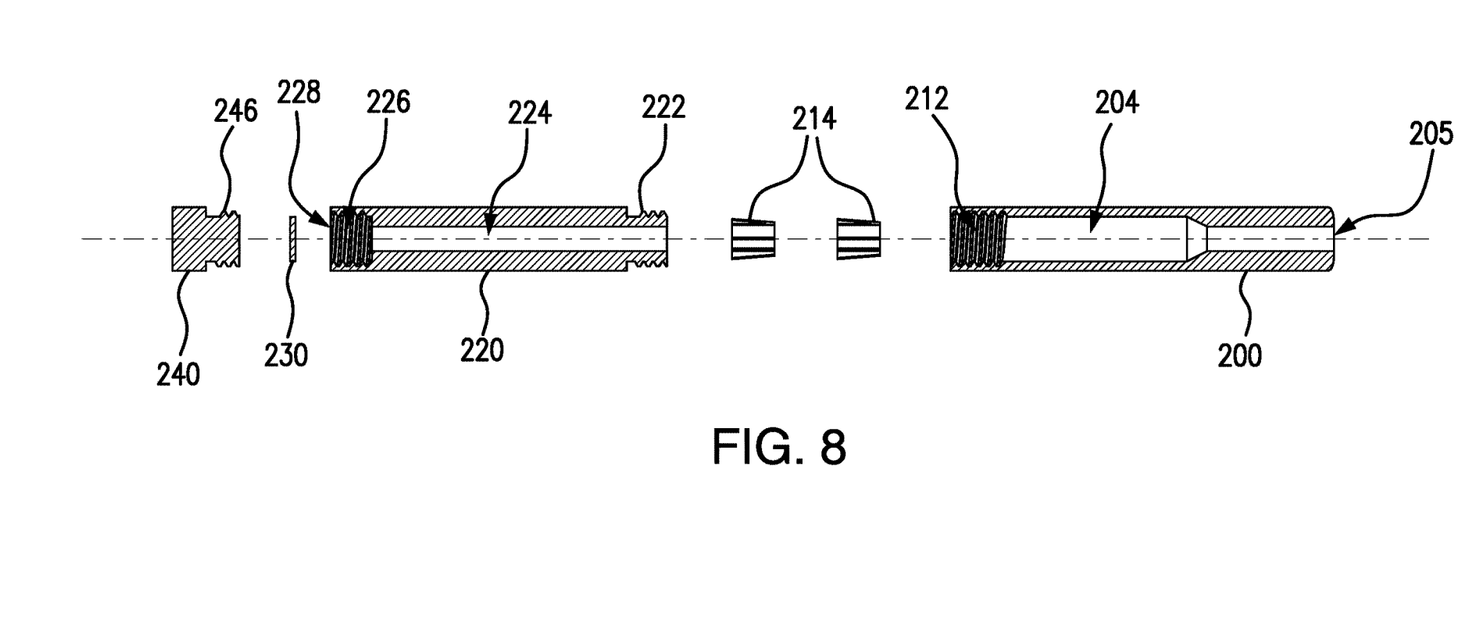
FIG. 8 is an exploded cross-sectional view of an embodiment of a pipette administration device.

An embodiment of a pipette is illustrated in FIG. 8 as an exploded cross-sectional view. In some embodiments, the aeration and filtration chamber 200 may comprise a mouthpiece and inhalation hole 205. In some embodiments, the mouthpiece and inhalation hole 205 may have a narrow inner diameter that opens to a region having a wider inner diameter, said region being a filter chamber 204. The filter chamber may be designed to have any appropriate or desirable dimensions in order to accommodate a filter. In some embodiments, one or more filters 214 may be inserted into the filter chamber. In some embodiments, the filter 214 may be a piece or portion of filtration material. In some embodiments, the filter 214 may be a canister or other filter insertable into the filter chamber 204. It can be appreciated than any filter usable for providing a cleaner inhalation to the patient or user is contemplated and may vary depending upon the combustible medicament that is being used.

In some embodiments, an aeration and filtration chamber 200 may comprise, at its end opposite the mouthpiece and inhalation hole, a threaded region 212 for engagement with the pipette front half 220. In some embodiments, the pipette front half 220 may have, at one end, threads 222 for engagement with the threads 212 of the aeration and filtration chamber 200. In some embodiments, the pipette front half 220 may have a continuous channel 224 through its length. In some embodiments, the channel 224 connects with the filtration chamber 204 when assembled. In some embodiments, the channel 224 may have one or more stepped or chamfering regions of various diameters. In some embodiments, the channel 224 may have a single diameter through its length opening to the base of the bowl 228.

In some embodiments, the bowl 228 may comprise a notch or region at its base configured to accept a filter screen 230. In some embodiments, the filter screen 230 is pressed into place at the base of the bowl 228. In some embodiments, the filter screen 230 is removable, cleanable, replaceable, and/or disposable. In some embodiments, the filter screen 230 is metal or another heat-resistant material safe for use with a combustible medicament. In some embodiments, the filter screen 230 retains and supports the combustible medicament before, during, and after its combustion. In some embodiments, the filter screen 230 prevents most or all of the solid portions of the combustible medicament from passing through it before, during, and after use and/or combustion and inhalation.

Figure 9:
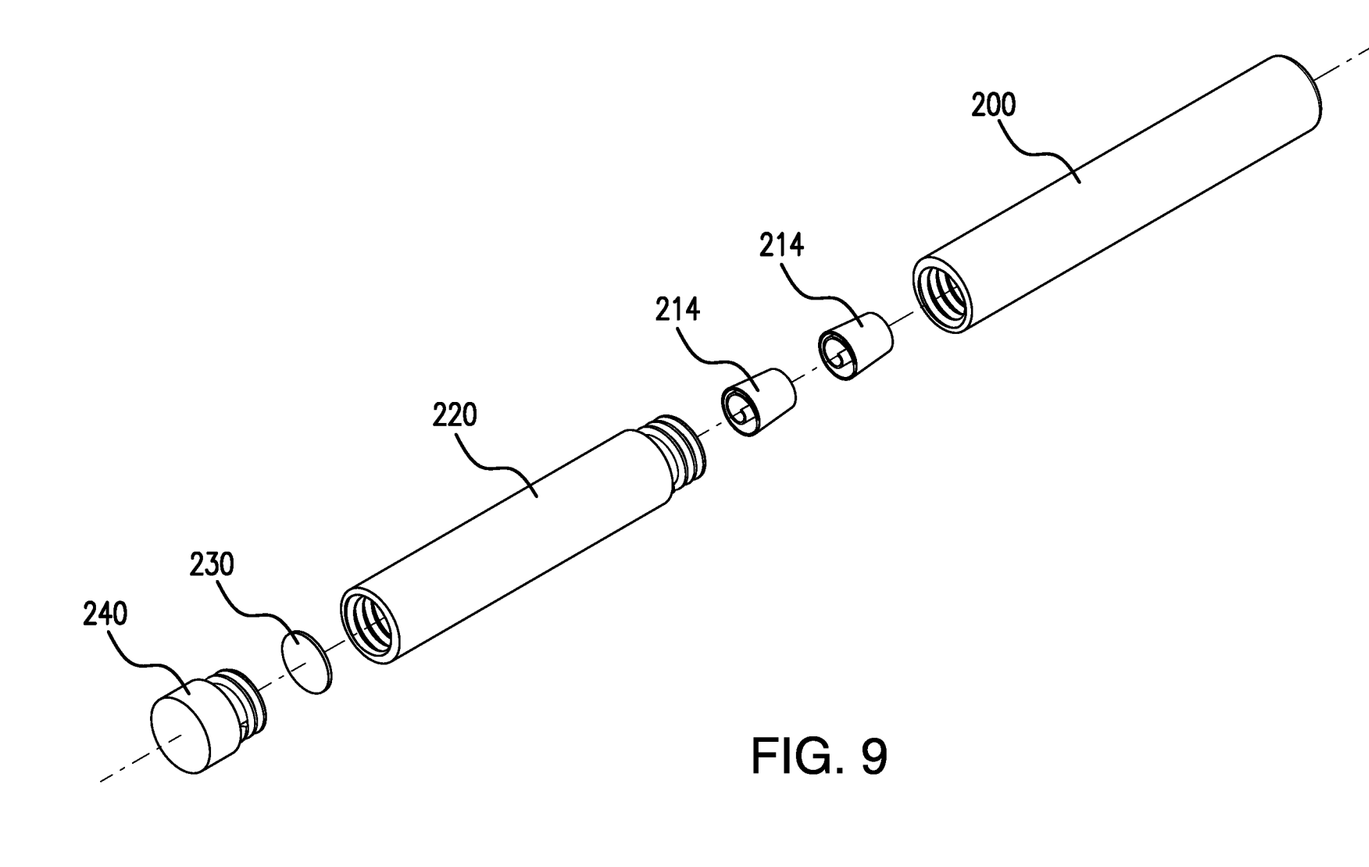
FIG. 9 is an exploded perspective view of an embodiment of a pipette administration device.

In some embodiments, the bowl is partially or fully defined by a rim 226. In some embodiments, the rim 226 is threaded for engagement with the cap 240. In some embodiments, the cap 240 comprises threads for threaded engagement with the threads of the rim 226 of the pipette front half 220. An exploded perspective view of an embodiment of the pipette is illustrated in FIG. 9.

In some embodiments, the pipette front half 220 has an outer diameter of from about 5 mm to about 20 mm, or from about 7 mm to about 12 mm, or from about 8 mm to about 12 mm, or from about 9 mm to about 11 mm, or from about 9 mm to about 10 mm. In some embodiments, the pipette front half 220 has an outer diameter of about 5 mm, or about 5.5 mm, or about 6 mm, or about 6.5 mm, or about 7 mm, or about 7.5 mm, or about 8 mm, or about 8.5 mm, or about 9 mm, or about 9.5 mm, or about 10 mm, or about 10.5 mm, or about 11 mm, or about 11.5 mm, or about 12 mm, or about 12.5 mm, or about 13 mm, or about 14 mm, or about 15 mm, or about 16 mm, or about 17 mm, or about 18 mm, or about 19 mm, or about 20 mm.

In some embodiments, the depth, from the front edge of the administration bowl 228 to the screen 230 is from about 3 mm to about 30 mm, or from about 4 mm to about 20 mm, or from about 5 mm to about 10 mm, or from about 6 mm to about 8 mm. In some embodiments, the depth, from the front edge of the administration bowl 228 to the screen 230, is about 3 mm, or about 3.5 mm, or about 4 mm, or about 4.5 mm, 5 mm, or about 5.5 mm, or about 6 mm, or about 6.5 mm, or about 7 mm, or about 7.5 mm, or about 8 mm, or about 8.5 mm, or about 9 mm, or about 10 mm, or about 12 mm, or about 14 mm, or about 15 mm, or about 20 mm, or about 25 mm, or about 30 mm.

The pipette administering and inhaling apparatus can be made with surgical steel or with steel commonly and intended for combustible use, aircraft grade aluminum and other materials not mentioned. Portions of the pipette having limited heat exposure may be made with materials different from portions having heat exposure. It can be appreciated that any appropriate materials known in the art are contemplated.

Systems

A dispensing mill and one or more administration devices may comprise a system for administration of a dosed amount of a combustible medicament. Systems may further comprise other components such as a push-pin or bore cleaner and filters. Systems may further comprise any further necessary or desirable components. Systems may further comprise medical equipment for monitoring the patient's status due to the administered dose or due to any other condition. Systems may have or involve substituted or alternative components such that any embodiment of the present disclosure is useful therewith.

In some embodiments, the dimensions of the mill and the dimensions of the pipe or pipette are configured for use with each other. In some embodiments, the dimensions of the dispensing chamber 125, such as its depth and diameter, are configured according to the dimensions of the pipette, such as its outer diameter and administration bowl 228 depth. In some embodiments, the dispensing chamber 125 has a diameter from about 8 mm to about 15 mm and a depth, from the surface of the top chamber 126 to the screen 130, from about 4 mm to about 8 mm, while the pipette front half 220 has an outer diameter from about 5 mm to about 13 mm and a depth, from the front edge of the administrating bowl 228 to the screen 230, from about 4 mm to about 8 mm.

In some embodiments, the dispensing chamber 125 has a diameter of about 11.1 mm and a depth, from the surface of the top chamber 126 to the screen 130, of about 6.4 mm, while the pipette front half 220 has an outer diameter of about 9.5 mm and a depth, from the front edge of the administrating bowl 228 to the screen 230, of about 6.4 mm.

Methods of Use

Provided for are methods of using the apparatuses, devices, and systems of the present disclosure. Particularly, the embodiments described may be useful for accurately and consistently delivering a prescribed, measured, or desired dosage of a combustible medicament to a patient in need thereof. The described embodiments are representative and may be combined in any advantageous or desired manner with described or existing apparatuses, devices, and systems.

In some embodiments, methods of use may begin with assembly of a pipette such as that of FIG. 9. The aeration and filtration chamber 200 may be first prepared by insertion of one or more filters 214. In some embodiments, a push-pin and bore cleaner (may be referred to alternatively as "push-pin" or "bore cleaner") may be configured to assist in the insertion of one or more filters 214 before use and removal of the one or more filters 214 after one or more uses. In an embodiment, the push-pin has a rod shape dimensioned to insertably fit into the smallest diameter of the pipette. In some embodiments, the push-pin may terminate at one end with a larger, rounded end configured to fit within the aeration and filtration chamber 200 in order to assist with insertion of one or more filters 214. The larger, rounded end may have a wide, semi-rounded flat head. The push-pin may also be used for any other purpose for which its dimensions may be advantageous, such as in the insertion and/or removal of the filter screen 230 from the end 226 of the pipette front half 220. In some embodiments, one or more filters 214 may be inserted into the aeration and filtration chamber 200. In some embodiments, two, or three, or four, or five filters may be inserted into the aeration and filtration chamber 200. In some embodiments, no filters may be inserted into the aeration and filtration chamber 200.

An embodiment of a filter may be a spiraled frustoconical filter of a rolled paper material as illustrated in FIG. 9. Spiraled frustoconical filters may comprise a golden ratio or Fibonacci spiral. A spiraled frustoconical filter may remove impurities without disrupting the airflow as the smoke from the combusted medicament is inhaled. Such a spiral design may utilize centrifugal forces borne from inhalation to maximize vapors and minimize waste. In some embodiments, more than one spiraled frustoconical filter is used. In some embodiments, three spiraled frustoconical filters are used. In some embodiments, two spiraled frustoconical filters are used. In some embodiments, a filter may be any appropriate filter that is configured or can be configured to fit within the aeration and filtration chamber 200 while providing sufficient aeration for the inhalation of the combustible medicament once it is combusted.

Once the aeration and filtration chamber 200 has been prepared with any inserted filters, if present, the aeration and filtration chamber 200 may be threadably engaged with the pipette front half 220. The pipette front half 220 may be threadably engaged with the cap 240 which may function to provide a scent-blocking seal in-between uses. The cap 240 may be referred to as a "scent-seal lock-cap" or similar phrases. If the cap 240 is present, it may be removed to access the administering bowl 228. At this stage, a filter screen 230 may be inserted into its position at the base of the administering bowl 228. If a filter screen 230 is already inserted from a prior use, it may be optionally removed and cleaned, or may be left in place for the next use. With the aeration and filtration chamber 200, prepared with any inserted filters, engaged with the pipette front half 220 having a filter screen 230 installed, the pipette is ready for use alone or in combination with a milling device.

The milling device may be used to prepare a dosage of a combustible medicament for use. With the device assembled as illustrated in FIG. 1, and as described in the present disclosure, the mill top plate 100 may be removed from the assembly and, in particular, may be disengaged from the mill bottom plate 110. The combustible medicament may then be placed within the mill for grinding. In practice, the combustible medicament may be pressed into the mill blades of the mill bottom plate 110 while being careful to keep the central magnetic engagement area substantially clear of combustible medicament. Once the combustible medicament is placed in the mill, the mill top half is pressed onto the mill bottom plate 110. Pressure and/or twisting of the mill top plate with respect to the rest of the assembly may be required to fully engage the mill top plate 100 with the mill bottom plate 110 due to the presence of the combustible medicament. The pressure and/or twisting will lead to grinding of the combustible medicament to some extent. Further grinding may be necessary or desired once the mill top plate 100 and mill bottom plate 110 are magnetically engaged. Grinding is complete once the combustible medicament has been ground to a sufficiently small size in order to fall through the holes 115 of the mill bottom plate 110.

The size of the holes 115 may be an important feature for the dosing of the combustible medicament. The size of the holes ultimately dictate the size of combustible medicament pieces that pass through to the dispensing chamber 125. By altering the size of the pieces, the packing of the combustible medicament particles within the dispensing chamber 125 may be altered, thereby altering the administered dose. In some embodiments, certain mill bottom plates 110 may be used or prescribed for use with a certain combustible medicament. In some embodiments, a mill bottom plate 110 may be universal for one or more combustible medicaments. In some alternative embodiments, pieces of combustible medicament that do not fall through the holes 115 may be manually removed from the mill and transferred to the dispensing chamber 125 for a manual dosing usage.

Figure 10:
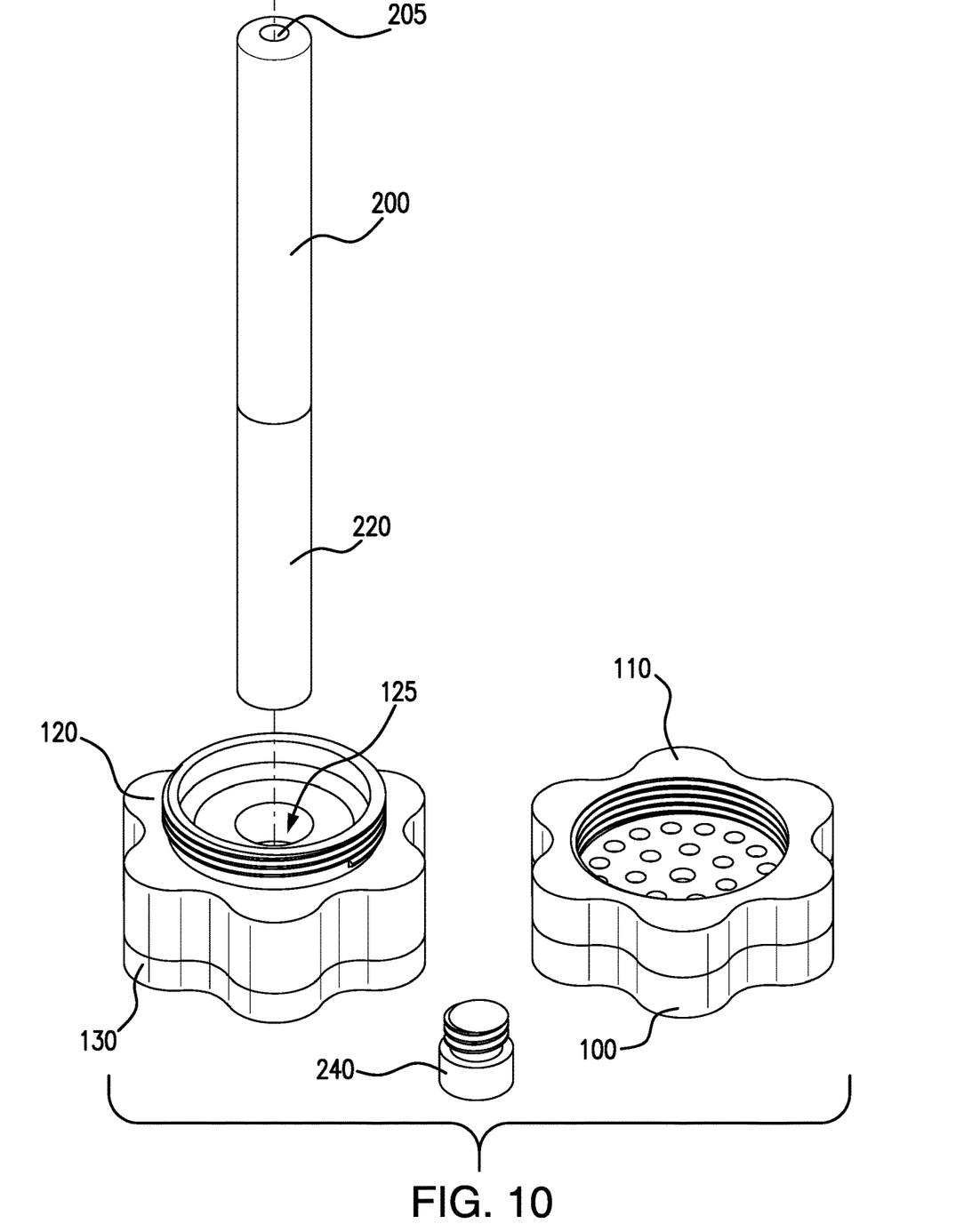
FIG. 10 is a perspective view of an embodiment of a milling and dispensing device in use with an embodiment of a pipette administration device.

Once the combustible medicament has fallen through the holes 115 of the mill bottom plate 110 into the dispensing chamber 125, the mill may be partially disassembled as illustrated in FIG. 10 for dispensing the ground combustible medicament. The ground combustible medicament will be, at this stage, held within the dispensing chamber 125.

In an embodiment, as illustrated in FIG. 10, an assembled pipe or pipette and, particularly, the administration bowl 228 thereof, is utilized for formulating the dosage in conjunction with the dispensing chamber 125. The assembled pipe or pipette is then used for administering the dose to the patient. As illustrated in FIG. 10, the pipette, with its cap 240 removed, is aligned with the dispensing chamber 125 such that the administering bowl 228 is positioned to accept ground combustible medicament when pressed into the dispensing chamber.

Figure 11:
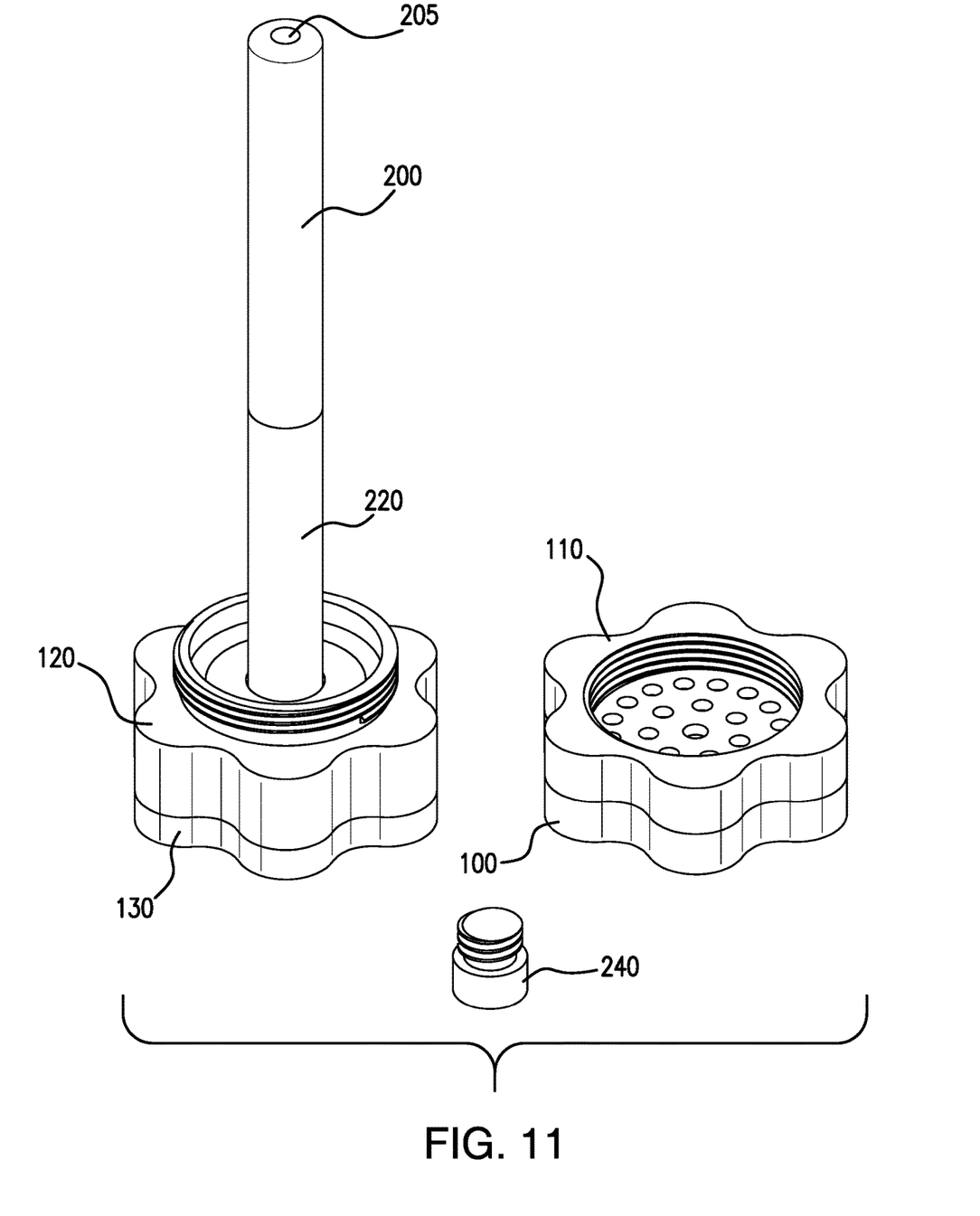
FIG. 11 is a perspective view of an embodiment of a milling and dispensing device in use with an embodiment of an administration device, where the pipette administration device is inserted into the dosage dispensing chamber of the milling and dispensing device.

As illustrated in FIG. 11, the pipette is inserted into the dispensing chamber 125 thereby pressing ground combustible medicament into the administering bowl 228 to formulate the dosage. In some embodiments, the pipette is pressed with an appropriate amount of pressure and, optionally, with a twisting motion in order to press ground combustible medicament into the administering bowl 228. Once the dosage has been formulated within the administration bowl 228, it is ready for administration to the patient. In some embodiments, all of the ground combustible medicament in the dispensing chamber 125 may be pressed into the administering bowl 228 in one use. In other embodiments, only a portion of the ground combustible medicament may be pressed into the administering bowl 228 in one use and remaining combustible medicament may be used in further and/or future doses.

Several alternative embodiments are contemplated. In some alternative embodiments, the administering bowl 228 measures or determines the dosage. In some alternative embodiments, the dispensing chamber 125 measures or determines the dosage. In an alternative embodiment, a desired dosage is achieved once the combustible medicament is level with the top of the dispensing chamber 125. In some alternative embodiments, the dispensing chamber 125 may alternatively have one or more etchings or markings along its inner perimeter to denote one or more dosages. In some alternative embodiments, the combustible medicament may be lightly agitated and/or packed into the dispensing chamber 125 for settling of the ground combustible medicament for accurate dosing. In some embodiments, if too much ground combustible medicament is present, a portion may be removed such that the correct dosage is measured.

In some alternative embodiments, all of the ground combustible medicament may be pressed into the administering bowl 228 in one use. In other alternative embodiments, only a portion of the ground combustible medicament may be pressed into the administering bowl 228 in one use and repeat steps may be required to complete the dosage. As would be understood to a person of skill in the art and/or patient, such repeat steps would be accomplished by combusting and administering a first dispensed portion of the dose, followed by removal of the spent combustible medicament from the administering bowl 228. The pipette may then be cleaned and/or directly re-used with the dispensing chamber 125 in order to press a second dispensed portion of the dose into the dispensing chamber 125 for use. It can be appreciated that any intermediary cleaning steps may interspersed in the usage methods, including replacement and/or checking of filters, such that the patient experiences the desired inhalation experience of the dose. Once the dosage has been fully removed from the dispensing chamber 125, the patient may then repeat the above steps for obtaining a second dose, if necessary, desired, or prescribed.

Any cleaning steps may include isopropyl alcohol, acetone, or any suitable solvent. Isopropyl alcohol of at least 60% alcohol or greater may be desirable in some embodiments. Cleaning steps may involve soaking, scrubbing, replacement of replaceable pieces, or any other desired or necessary steps. Equivalent steps are contemplated and useful where appropriate.

Methods of Treatment

Methods of treatment involve any usage of a dosage of a combustible medicament for administration to a subject in need or desire thereof. In some embodiments, a patient may be suffering from any psychological, physical, or neurologic disorder. Methods of treatment may be accomplished using the pipette device of the present invention or any appropriate device.

Once the combustible medicament has been dosed, prepared for administration, and inserted, placed, or otherwise held within an administration device, the combustible medicament may be ready for use. Use is typically accomplished by burning or combusting the combustible medicament with an open flame until sufficient combustion is achieved. Such sufficient combustion would be recognized by a person of skill in the art or by a patient. Sufficient combustion may be observed and taught by a physician. During the combustion process, the patient may inhale so that the smoke or vapors of the combustible medicament are inhaled into the lungs of the patient. The air volume displaced by the patient's lungs may have a bearing on the speed and amount of combustion and the administration may be, at least initially, observed by a trained physician. Once a desired amount of medicament smoke or vapor has been inhaled, the patient may hold the smoke or vapor in their lungs for a desired period or time, as desired, necessary, or prescribed, followed by exhaling the smoke. If desired, necessary, or prescribed, the combustion and inhalation process may be repeated until the combustible medicament in the administration device is burned or spent. If desired, necessary, or prescribed, the burned or spent combustible medicament may be removed from the administration device, which may be further cleaned if desired or necessary. Typically, the method of treatment may be followed until a desired therapeutic outcome has been achieved or until the dosage has been fully used.

In some embodiments, a dosage may be enhanced or supplemented by usage of kief collected in the kief collection chamber after passing through the screen at the base of the dispensing chamber 125. The kief may be mixed with or placed directly on a dose prior to administration. The kief may be dosed by volume, mass, or any appropriate method. Kief may be used as prescribed, desired, or otherwise.

I claim:

1. A system for dispensing a prescribed dosage of a botanical medicament for vaporization, the system comprising:
    a dosing and dispensing apparatus, including:
    a top mill plate including one or more blades arranged around its center, said blades disposed in a cavity defined by an outer rim and a base;
    a bottom mill plate rotatably engageable with said top mill plate, the bottom mill plate including one or more blades arranged around its center, wherein said blades are disposed in a cavity defined by an outer rim and a base having one or more holes continuous therethrough;
    a ground flower canister engageable with the bottom mill plate;
    a dosage dispensing chamber formed as a continuous cylindrical cavity extending through the ground flower canister in its axial dimension, the dosage dispensing chamber defining an insertion axis for receiving an administration device, wherein the insertion axis is collinear with a centerline extending through the center of the dosage dispensing chamber;
    a kief extractor screen that bounds the dosage dispensing chamber at an end thereof and defines a chamber depth, the kief extractor screen configured to retain at least a portion of milled botanical medicament; and
    a kief extract canister engageable with the ground flower canister, the kief extractor screen disposed therebetween, and having a cavity defined by an outer rim and a base; and
    the administration device including:
    a cylindrical rear segment having a continuous bore therethrough and proximal rear and front ends, said rear segment bore having a smaller diameter at the proximal rear end and opening to a larger diameter to form a filter chamber extending to the proximal front end;
    a cylindrical front segment engageable with the rear segment and having a continuous bore therethrough and distal rear and front ends, said front segment bore having a smaller diameter at the distal rear end and opening to a larger diameter to form an administration bowl extending to the distal front end; and
    a filter screen removably insertable into and forming a bottom of the administration bowl,
    wherein the administration bowl is so dimensioned as to be insertable into the dosage dispensing chamber exclusively along the insertion axis and the dosage dispensing chamber is configured to receive the administration bowl solely along the insertion axis,
    wherein insertion of the administration bowl into the dosage dispensing chamber to the chamber depth defined by the kief extractor screen defines a predetermined dosage of milled botanical medicament within the administration bowl.

2. The system of claim 1, wherein the dosage dispensing chamber of the dosing and dispensing apparatus has a diameter of between about 8 mm and about 15 mm and a depth, from a top surface of the ground flower canister to the kief extractor screen, of between about 4 mm and about 8 mm; and wherein the cylindrical front segment of the administration device has an outer diameter of between about 5 mm and about 13 mm and a depth, from the distal front end of the administration bowl to the filter screen, of between about 4 mm and about 8 mm.

3. The system of claim 2, wherein the dosage dispensing chamber of the dosing and dispensing apparatus has a diameter of about 11.1 mm and a depth, from the top surface of the ground flower canister to the kief extractor screen, of about 6.4 mm; and wherein the cylindrical front segment of the administration device has an outer diameter of about 9.5 mm and a depth, from the distal front end of the administration bowl to the filter screen, of about 6.4 mm.

4. The system of claim 1, wherein the top mill plate comprises a centered protrusion having a magnet and the bottom mill plate comprises a centered magnet, and wherein the top mill plate and bottom mill plate are magnetically engageable.

5. The system of claim 1, wherein the blades of the top mill plate and the blades of the bottom mill plate are arranged concentrically and are non-interfering when the top mill plate and bottom mill plate are engaged.

6. The system of claim 1, wherein the ground flower canister is threadably engageable with the bottom mill plate, and wherein the kief extract canister is threadably engageable with the ground flower canister.

7. The system of claim 1, wherein the dosage dispensing chamber has a diameter of between about 8 mm and about 15 mm and a depth, from a top surface of the ground flower canister to the kief extractor screen, of between about 4 mm and about 8 mm.

8. The system of claim 1, wherein each of the top mill plate, bottom mill plate, ground flower canister, and kief extract canister have an outer perimeter on which one or more protrusions and/or depressions are disposed.

9. The system of claim 8, wherein each of the top mill plate, bottom mill plate, ground flower canister, and kief extract canister have six protrusions.

10. The system of claim 1, wherein the cylindrical rear segment and cylindrical front segment are threadably engageable.

11. The system of claim 1, wherein the cylindrical front segment has an outer diameter of between about 5 mm and about 13 mm and a depth, from the distal front end of the administration bowl to the filter screen, of between about 4 mm and about 8 mm.

12. The system of claim 1, wherein the filter chamber is so dimensioned as to accept one or more filters.

13. The system of claim 12, wherein the one or more filters comprise spiraled cellulose paper in a frustoconical shape.

14. The system of claim 13, wherein the spiraled frustoconical filters comprise a golden ratio or Fibonacci spiral.

15. The system of claim 14, wherein the filters are made of unrefined cotton or plant based cellulose.

16. The system of claim 1, further comprising a helical thread provided on an inner side wall of the administration bowl, said thread configured to draw in milled botanical medicament from the dosage dispensing chamber into the administration bowl via a twisting motion.

17. The system of claim 16, further comprising a cap provided with a screw thread removably engageable with the helical thread on the inner side wall of the administration bowl.

18. The system of claim 1, further comprising a retaining washer that supports and retains the kief extractor screen against the bottom surface of the ground flower canister, wherein the retaining washer prevents displacement of the kief extractor screen that would alter the defined depth of the dispensing chamber.

19. The system of claim 1, wherein the administration device is made of surgical steel.

* * * * *